United States Patent [19]
Feltham et al.

[11] Patent Number: 5,513,986
[45] Date of Patent: May 7, 1996

[54] INTRAORAL DENTAL APPARATUS

[75] Inventors: Erika B. Feltham, 1417 Knoll Park La., Fallbrook, Calif. 92028; James P. Stewart, Escondido, Calif.

[73] Assignee: Erika B. Feltham, Fallbrook, Calif.

[21] Appl. No.: 276,641

[22] Filed: Jul. 19, 1994

Related U.S. Application Data

[63] Continuation of Ser. No. 140,791, Oct. 21, 1993, abandoned.

[51] Int. Cl.$^6$ .......................... A61C 17/06; A61C 17/14
[52] U.S. Cl. ................................. 433/91; 433/93
[58] Field of Search .................. 433/91, 93, 94, 433/80, 68, 71, 34, 43, 216; 601/164; 604/77

[56] References Cited

U.S. PATENT DOCUMENTS

| | | | |
|---|---|---|---|
| 2,937,445 | 5/1960 | Erickson | 433/93 |
| 3,049,806 | 8/1962 | Cofresi | 433/93 |
| 3,527,218 | 9/1970 | Westine | 433/80 |
| 3,566,869 | 3/1971 | Crowson | 433/80 |
| 3,731,675 | 5/1973 | Kelly | 128/62 A |
| 4,560,351 | 12/1985 | Osborne | 433/80 |
| 4,802,851 | 2/1989 | Rhoades | 433/93 |
| 4,992,046 | 2/1991 | Sharp | 433/91 X |
| 5,018,967 | 5/1991 | Schwalbach | 433/91 X |
| 5,104,315 | 4/1982 | McKinley | 433/80 |

FOREIGN PATENT DOCUMENTS

| | | | |
|---|---|---|---|
| 314477 | 9/1919 | Germany | 433/93 |
| 204376 | 4/1939 | Switzerland | 433/91 |

OTHER PUBLICATIONS

Product Catalog of American Dental Accessories, Inc., Summer 1993, showing bite registration trays, fluoride gel trays, and impression trays on p. 40.

Primary Examiner—Nicholas D. Lucchesi
Attorney, Agent, or Firm—Loyal M. Hanson

[57] ABSTRACT

A dental apparatus includes a tray that is shaped and dimensioned to fit over at least some of the teeth of a patient. The tray defines a tunnel through which to evacuate saliva from the mouth of the patient. The tray includes a connector portion for coupling a suction source to the tunnel, and the tray defines at least a first opening in fluid communication with the tunnel through which saliva may be sucked from the mouth of the patient into the tunnel for communication to the suction source. The apparatus may take the form of a fluoride treatment tray or an impression tray, including a bite registration tray, it may include multiple trays, and it may define additional spaced-apart openings in fluid communication with the tunnel to facilitate evacuation of saliva from a larger region within the mouth of the patient. Preferably, the connector portion is configured to receive an end of a conventional saliva ejector in a close fitting relationship in order to couple a commonly used suction source to the tunnel. In one version, the tray is formed from two layers of transparent material to facilitate viewing of saliva being evacuated through the tunnel. A dental apparatus for isolating a field within the mouth of a patient is also disclosed that includes an integral saliva evacuation tunnel.

7 Claims, 4 Drawing Sheets

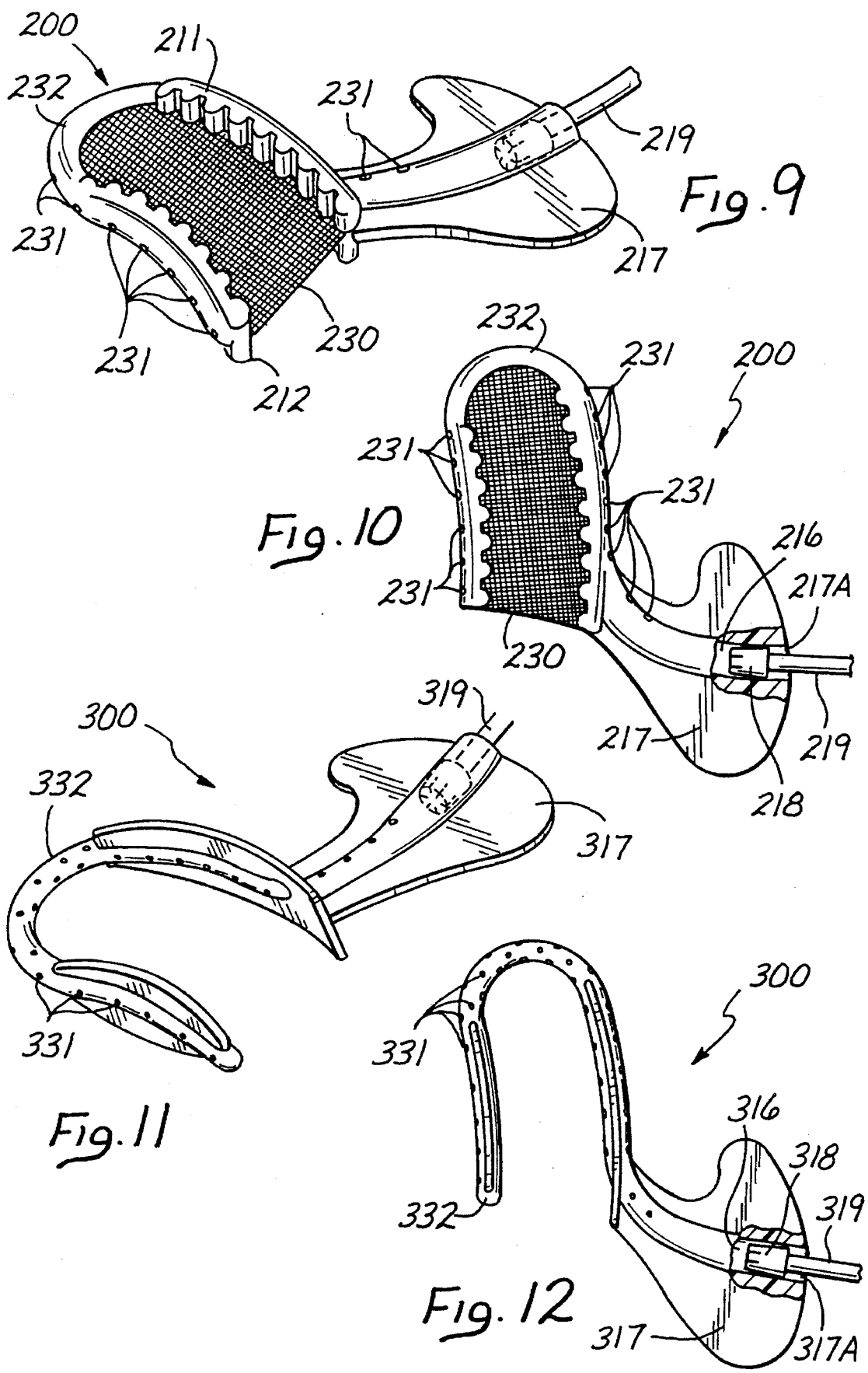

INTRAORAL DENTAL APPARATUS

This application is a continuation of application Ser. No. 08/140,791 filed Oct. 21, 1992, now abandoned.

BACKGROUND OF THE INVENTION

1. Technical Field

This invention relates generally to dental equipment, and more particularly to an intraoral dental apparatus with increased functionality.

2. Description of the Prior Art

Recall that many dental procedures have the dental professional place a fluoride tray, impression tray, bite registration tray, or other object (i.e., an intraoral dental apparatus) into the patient's mouth. The intraoral apparatus facilitates the procedure undertaken. However, it also stimulates the salivary process sufficiently to cause some problems.

Consider a typical fluoride treatment. The dental professional places a fluoride tray filled with an acidulated fluoride composition into the patient's mouth. That is done to hold the substance in contact with the teeth for several minutes. During that period, however, the fluoride tray causes significant salivation that the taste of the acidulated fluoride composition only increases.

The dental professional has instructed the patient not to swallow during the procedure because swallowing some of the fluoride composition might cause vomiting or other undesired effects. Hopefully, the saliva pools beneath the tongue where the dental professional has placed a saliva ejector in order to evacuate it. But saliva from the parotid glands and others often do not pool as desired and so the saliva ejector must often be moved around the mouth while the fluoride tray is in place. Doing so can be inconvenient and insufficient.

One might describe the problem as inadequate evacuation of saliva during use of the fluoride tray. The same problem exists in varying degrees with other intraoral apparatuses. A saliva ejector helps, but it must be carefully positioned, held in place, and sometimes moved to whatever unexpected region which the saliva pools. Furthermore, some apparatuses (e.g., impression trays) leave no room for a saliva ejector.

SUMMARY OF THE INVENTION

This invention solves the problems outlined above by providing a dental apparatus with an integral saliva-evacuation tunnel through which to evacuate saliva. A connector portion at one end of the tunnel couples it to a suction source (e.g., the distal end of a conventional saliva ejector). One or more openings advantageously positioned along the tugel enable saliva at critical regions within the mouth to be sucked into the tunnel for communication to the suction source. Thus, the invention not only keeps the saliva ejector out of the mouth, it also improves saliva evacuation.

In terms of the claim language that is subsequently developed, a dental apparatus for fluoride treatment includes a lower tray for holding a fluoride composition in contact with at least some of the lower teeth of the patient. According to a major aspect of the invention, the lower tray defines a tunnel through which to evacuate saliva from the mouth of the patient. The lower tray includes a connector portion for coupling a suction source to the tunnel, and it defines at least one opening in fluid communication with the tunnel through which saliva may be sucked from the mouth of the patient into the tunnel for communication to the suction source.

Preferably, the connector portion is configured to receive the distal end of a conventional saliva ejector. In addition, the lower tray may define additional spaced-apart openings in fluid communication with the tunnel to facilitate evacuation of saliva from a larger region within the mouth of the patient. The lower tray may include connected first and second layers that are shaped to define the tunnel and the connector portion, and they may be composed of a transparent material to facilitate viewing of saliva being evacuated through the tunnel. An upper tray may be hinged to the lower tray to enable treatment of the upper teeth as well. Intraoral dental apparatuses with integral saliva evacuation tunnels are also described and claimed in the form of impression trays, bite registration trays, and a field isolation apparatus.

The foregoing and other objects, features, and advantages of the invention become more apparent upon reading the following detailed description with reference to the illustrative drawings.

BRIEF DESCRIPTION OF THE DRAWINGS

FIGS. 9 and 10 are three-dimensional and top views of a third intraoral dental apparatus that takes the form of a second version of a bite registration tray; and FIGS. 11 and 12 are three-dimension and top views of a fourth intraoral dental apparatus that takes the form of a field isolation apparatus.

DESCRIPTION OF THE PREFERRED EMBODIMENTS

Figure 1:
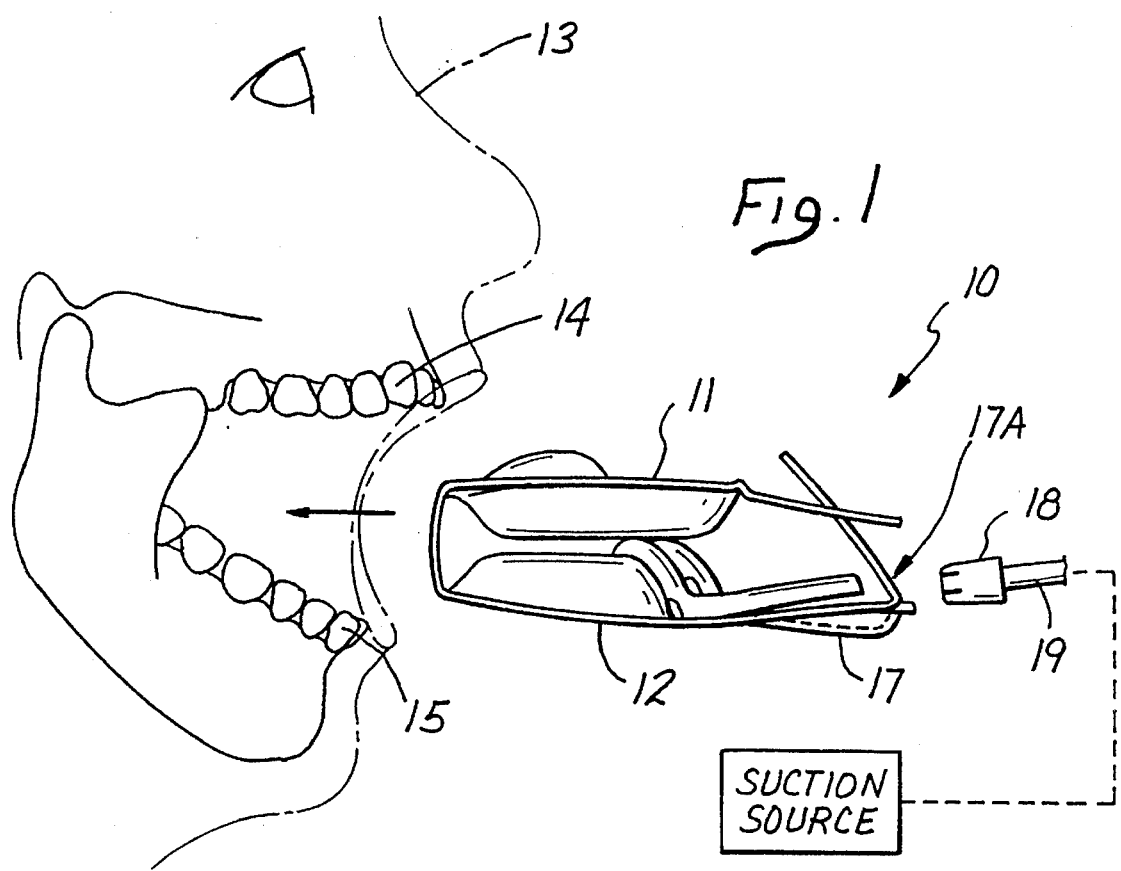
FIG. 1 of the drawings is a pictorial view of a first intraoral dental apparatus constructed according to the invention in the form of a fluoride tray that has been folded for placement into a the mouth of a patient.

FIGS. 1–6 of the drawings show various details of an intraoral dental apparatus constructed according to the invention. It takes the form of a fluoride tray 10 and it is similar in some respects to many existing fluoride trays (e.g., the hinged double fluoride trays available from American Dental Accessories, Inc. of Minneapolis, Minn. under the trademark CROSSTEX). It includes a first tray (sometimes called an upper arch tray) that is subsequently referred to as an upper tray 11 and a second tray (sometimes called a lower arch tray) that is subsequently referred to as a lower tray 12. The upper and lower trays 11 and 12 are hinged together and they are shaped and dimensioned to fit in the mouth of a patient 13 for fluoride treatment purposes.

The dental professional places some fluoride gel in each tray, folds the fluoride tray 10 into the folded configuration shown in FIG. 1, and then inserts it into the mouth of the patient 13. The patient 13 then closes his mouth with the result that the upper tray 11 holds the fluoride gel against the upper teeth 14 and the lower tray holds the fluoride gel against the lower teeth 15. The patient holds that position for several minutes to insure optimal fluoride assimilation. Then the dental professional removes and discards the fluoride tray 10.

Those steps are well known and they are usually accompanied by placement of a saliva ejector into the patient's mouth to evacuate saliva during the procedure. But unlike existing fluoride trays, the fluoride tray 10 includes an integral saliva evacuation tunnel 16 (FIGS. 4 and 5) designed to facilitate saliva evacuation. A connector portion 17 of the lower tray 12 (FIGS. 1–4 and 6) receives a distal end 18 of a conventional saliva ejector 19 (FIGS. 1 and 6) in order to couple a suction source to the tunnel 16. The connector portion 17 defines an opening 17A into which the distal end 18 fits in close fitting relationship for that purpose. The dental professional inserts the distal end 18 into the opening 17A either before or after placing the fluoride tray 10 in the patient's mouth.

A suction source illustrated in block diagram form in FIG. 1 may take any of various forms, including a known type of dental suction source. The saliva ejector 19 represents any of various saliva ejectors, including, for example, the six-inch long disposable saliva ejector tips available from American Dental Accessories, Inc. of Minneapolis, Minn. under the trademark CROSSTEX. Mating with that type of saliva ejector makes the fluoride tray 10 compatible with commonly used dental equipment. Of course, the lower tray 12 may be configured to otherwise couple a suction source to the tunnel 16 without departing from the broader inventive concepts disclosed.

The lower tray 12 defines at least a first opening 20 in fluid communication with the tunnel 16. Preferably, the first opening 20 occupies a position on the lower tray 12 such that it is disposed beneath the tongue when the fluoride tray 10 is in the patient's mouth. That placement promotes better evacuation of saliva pooling beneath the tongue.

Figure 2:
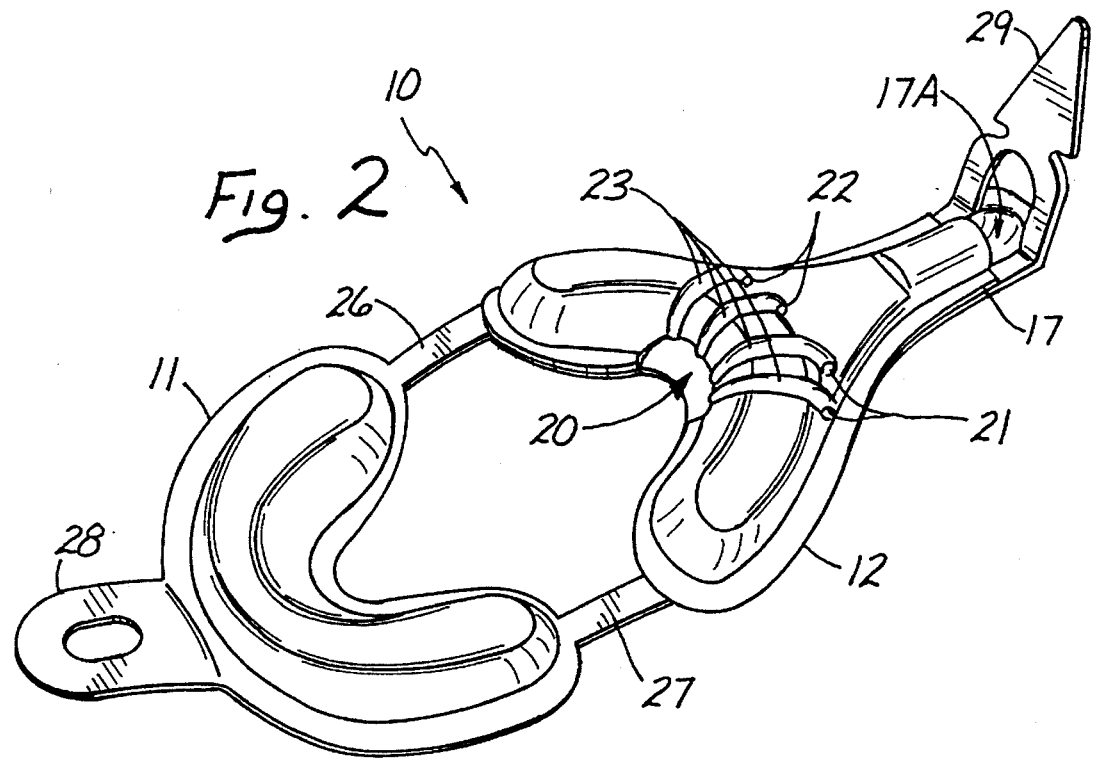
FIG. 2 is a somewhat enlarged three-dimensional view of the fluoride tray in an unfolded configuration.
Figure 3:
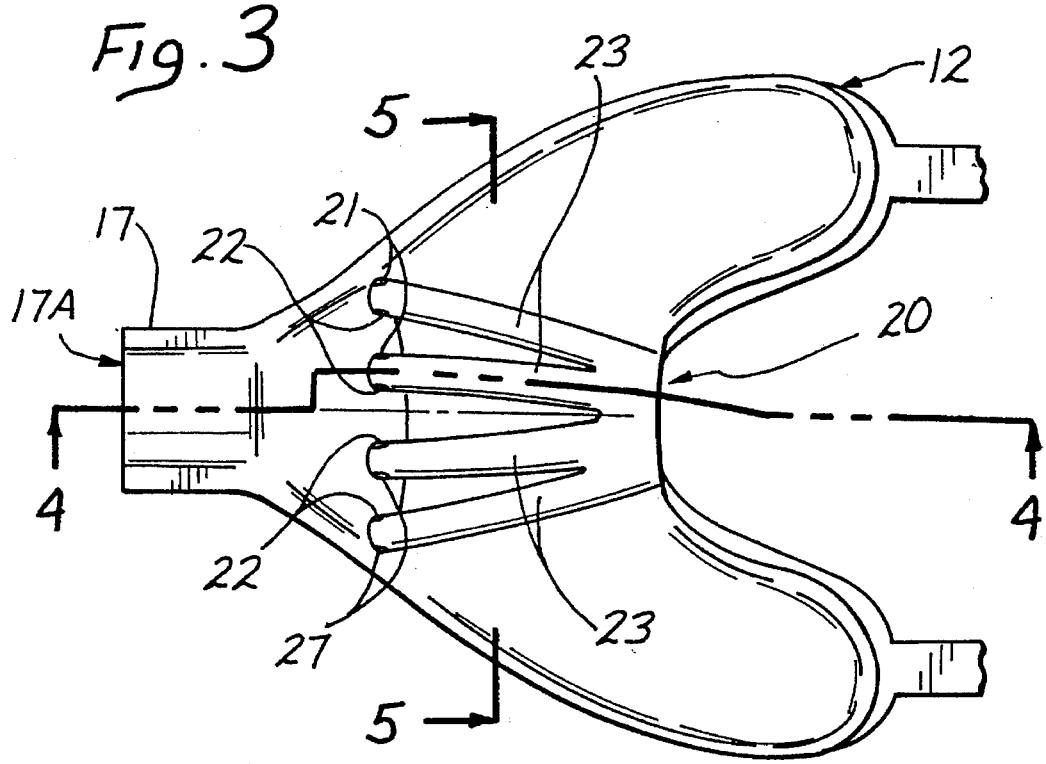
FIG. 3 is a further enlarged top view of the lower tray portion of the fluoride tray.
Figure 4:
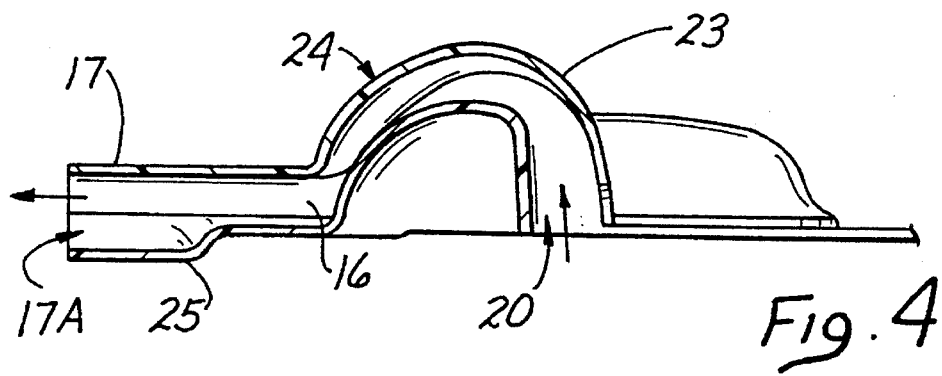
FIG. 4 is a cross sectional view of the fluoride tray taken on line 4—4 of FIG. 3.
Figure 5:
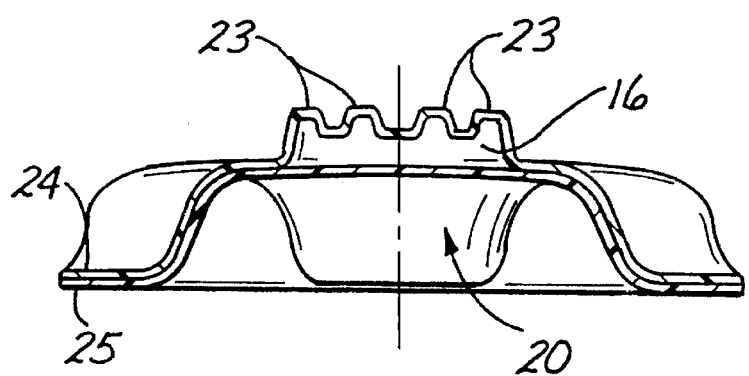
FIG. 5 is a cross sectional view of the fluoride tray taken on line 5—5 of FIG. 3.
Figure 6:
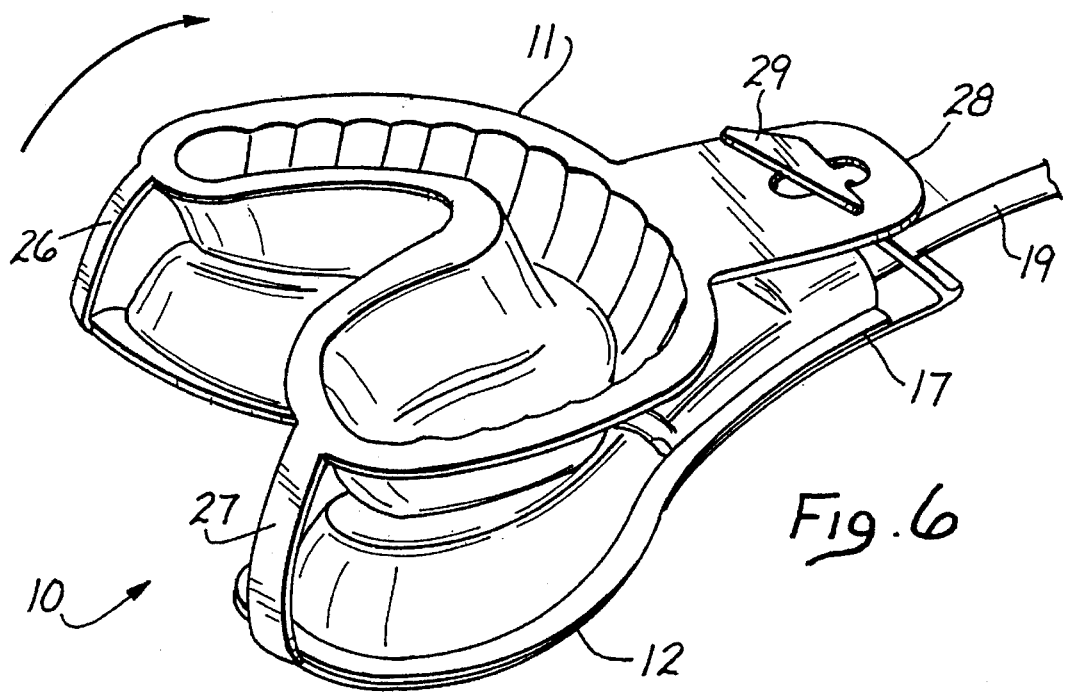
FIG. 6 is an enlarged three-dimensional view of the fluoride tray in the folded configuration.

The illustrated lower tray 12 also includes additional openings 21 along the distal aspects and 22 along the mesial aspects of four ribs 23 (FIGS. 2 and 3). They are in fluid communication with the tunnel 16 and serve to facilitate evacuation of saliva flowing from the parotid glands.

The ribs 23 help define the tunnel 16 while adding some rigidity to the lower tray 12. They are formed by suitable known means (e.g., molding) in a first layer 24 of transparent plastic (FIGS. 4 and 5) which is bonded by suitable known means to a second layer 25 of transparent plastic (e.g., by gluing). Hinge members 26 and 27 enable the dental professional to fold the fluoride tray 10 in the folded configuration shown in FIG. 6. A female fastener member 28 (an upper tray tab) cooperates with a male fastener member 29 (a lower tray tab) to retain the fluoride tray 10 in the folded configuration. Of course, the additional openings, ribs, multiple layers, hinges, and fastener members may all be omitted without departing from the broader inventive concepts disclosed. Furthermore, an apparatus with a single lower tray falls within the broader scope of the claims, although the fluoride tray 10 includes hinged together upper and lower trays.

Figure 7:
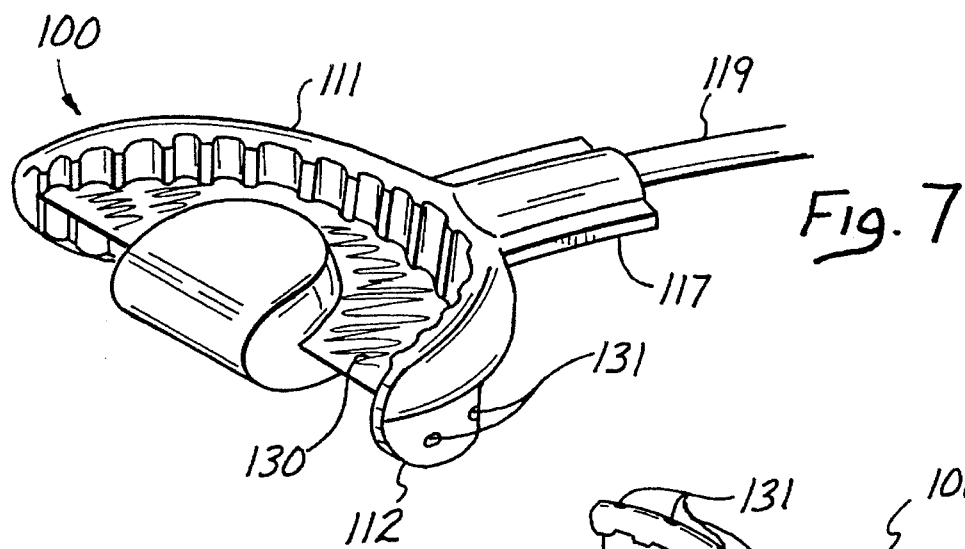
FIG. 7 is a three-dimensional view of a second intraoral dental apparatus that takes the form of a first version of a bite registration tray.
Figure 8:
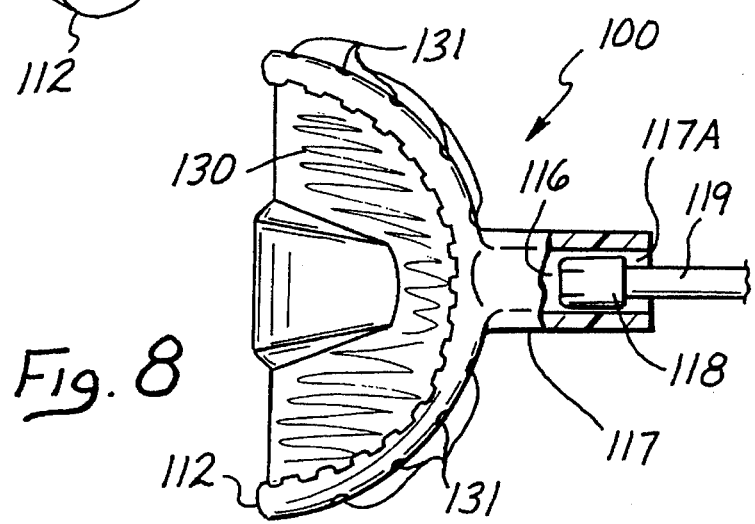
FIG. 8 is a bottom view of the first bite registration tray.

FIGS. 7 and 8 show various details of a second intraoral dental apparatus that takes the form of a first impression tray referred to as a double-sided bite registration tray 100. The bite registration tray 100 is similar in some respects to the fluoride tray 10 and only differences are discussed in further detail. For convenience, reference numerals designating parts of the bite registration tray 100 are increased by one hundred over those designating corresponding parts of the fluoride tray 10.

Like the fluoride tray 10, the bite registration tray 100 includes first and second trays designated upper and lower trays 111 and 112. They serve to hold a compound (sometimes called an impression material) in contact with the patient's teeth for bite registration and impression purposes, and they may be similar in some respects to corresponding parts of existing bite registration trays (e.g., the bite registration trays available from American Dental Accessories, Inc. under the trademark POLYBITE.

Unlike the fluoride tray 10, the upper and lower trays 111 and 112 of the bite registration tray 100 are fixed in the position shown in FIGS. 7 and 8, sharing a common tray bottom 130 composed of an open weave or other suitable material. Multiple openings 131 communicate saliva from the patient's mouth to an integral saliva evacuation tunnel 116 shown in the bottom view of FIG. 8. The openings 131 may be formed in one or both trays within the inventive concepts disclosed. A connector portion 117 defines an opening 117A into which the distal end 118 of a conventional saliva ejector 119 fits.

FIGS. 9 and 10 show various details of a third intraoral dental apparatus that takes the form of a second impression tray referred to as a bite registration tray 200. It is similar in some respects to the first bite registration tray 10 and, in some respects, to POLYBITE bite registration trays available from American Dental Accessories, Inc. Reference materials for corresponding parts are increased by one hundred over those of the first bite registration tray 100.

Upper and lower trays 211 and 212 share a common tray bottom 230, and multiple openings 231 in a common tray wall 232 (an elongated portion) communicate saliva from the patient's mouth to an integral saliva evacuation tunnel 216. The common tray wall 232 has a size and shape that fits in the mouth of a patient in a position such that it extends along the facial, buccal, and lingual aspects of some of the teeth of the patient. A connector portion 217 defines an opening 217A into which the distal end 218 of a saliva ejector 219 fits.

FIGS. 11 and 12 show still another intraoral dental apparatus constructed according to the invention in the form of an isolation tray 300. It may be used for isolating a field within the mouth of a patient. A single body of material has an elongated portion 332 and a connector portion 317. The elongated portion 332 has a size and shape that fits in the mouth of a patient in a position such that it extends along the facial, buccal, and lingual aspects of some of the teeth of the patient.

The elongated portion defines a tunnel 316 (FIG. 12) through which to evacuate saliva from the mouth of the patient. The connector portion 317 defines an opening 317A (a port) through which to couple a suction source to the tunnel (e.g., the distal end 318 of a saliva ejector 319), and the elongated member 332 defines a plurality of openings 331 in fluid communication with the tunnel 316 through which saliva may be sucked from the mouth of the patient into the tunnel 316 for communication to the suction source. Only a few of the openings 331 are designated.

Thus, the invention in all its embodiments provides a dental apparatus with an integral saliva-evacuation tunnel through which to evacuate saliva and, possibly, other dental materials, including amalgam shavings, phosphoric acid etching material, and so forth. A connector portion at one end of the tunnel couples it to a suction source (e.g., the distal end of a conventional saliva ejector). One or more openings advantageously positioned along the tunnel enable saliva at critical regions within the mouth to be sucked into the tunnel for communication to the suction source. In that way, the invention not only keeps the saliva ejector out of the mouth, it also improves saliva evacuation.

Although the foregoing description describes several exemplary embodiments, one of ordinary skill in the art may make many changes, modifications, and substitutions without necessarily departing from the spirit and scope of the invention. Any of various metal and plastic impression trays may be outfitted with an integral saliva evacuation tunnel within the scope of the following claims. What is claimed is:

What is claimed is:

1. A dental apparatus for fluoride treatment, comprising:
   means in the form of a lower tray for holding a fluoride composition in contact with at least some of the lower teeth of a patient;
   means in the form of an upper tray attached to the lower tray for holding a fluoride composition in contact with at least some of the upper teeth of the patient;
   the lower tray defining a tunnel through which to evacuate saliva from the mouth of the patient;
   the lower tray including means in the form of a connector portion for coupling a suction source to the tunnel; and
   the lower tray defining a plurality of openings in fluid communication with the tunnel through which saliva may be sucked from the mouth of the patient into the tunnel for communication to the suction source, said openings facing outwardly from the tray away and adapted to face from the teeth of the patient towards the tongue area of the patient;
   wherein the connector portion is configured to receive an end of a conventional saliva ejector in a close fitting relationship in order to couple a suction source to the tunnel;
   wherein the lower tray includes connected first and second layers that are shaped to define the tunnel and the connector portion; and
   wherein at least one of the first and second layers is at least partially composed of a transparent material to facilitate viewing of saliva being evacuated through the tunnel.

2. A dental apparatus for fluoride treatment, comprising:
   means in the form of a lower tray for holding a fluoride composition in contact with at least some of the lower teeth of a patient;
   means in the form of an upper tray attached to the lower tray for holding a fluoride composition in contact with at least some of the upper teeth of the patient;
   the lower tray defining a tunnel through which to evacuate saliva from the mouth of the patient;
   the lower tray including means in the form of a connector portion for coupling a suction source to the tunnel; and
   the lower tray defining a plurality of openings in fluid communication with the tunnel through which saliva may be sucked from the mouth of the patient into the tunnel for communication to the suction source, said openings facing outwardly from the tray and adapted to face away from the teeth of the patient towards the tongue area of the patient;
   wherein the lower tray includes connected first and second layers that are shaped to define the tunnel and the connector portion; and
   wherein at least one of the first and second layers is at least partially composed of a transparent material to facilitate viewing of saliva being evacuated through the tunnel.

3. A dental apparatus, comprising:
   means in the form of a tray that is shaped and dimensioned to fit over at least some of the teeth of a patient for holding a composition in contact with at least some of the teeth of a patient;
   the tray defining a tunnel through which to evacuate saliva from the mouth of the patient;
   the tray including means in the form of a connector portion for coupling a suction source to the tunnel; and
   the tray defining a plurality of openings in fluid communication with the tunnel through which saliva may be sucked from the mouth of the patient into the tunnel for communication to the suction source, some of said openings facing outwardly from the tray and adapted to face away from the teeth of the patient towards the tongue area of the patient, other ones of said openings being adapted to face away from the teeth of the patient towards the cheek area of the patient, and still other ones of said openings being adapted to face away from the teeth of the patient towards the lip area of the patient.

4. A dental apparatus, comprising;
   means in the form of a tray that is shaped and dimensioned to fit over at least some of the teeth of a patient for holding a composition in contact with at least some of the teeth of a patient;
   the tray defining a tunnel through which to evacuate saliva from the mouth of the patient;
   the tray including means in the form of a connector portion for coupling a suction source to the tunnel; and
   the tray defining a plurality of openings in fluid communication with the tunnel through which saliva may be sucked from the mouth of the patient into the tunnel for communication to the suction source, said openings facing outwardly from the tray and adapted to face away from the teeth of the patient towards the tongue area of the patient;
   wherein the tray includes connected first and second layers that are shaped to define the tunnel and the connector portion; and
   wherein at least one of the first and second layers is at least partially composed of a transparent material to facilitate viewing of saliva being evacuated through the tunnel.

5. A dental apparatus as recited in claim 4, wherein the connector portion is adapted structurally, to receive an end of a conventional saliva ejector in a close fitting relationship in order to couple a suction source to the tunnel.

6. A dental apparatus as recited in claim 4, wherein the apparatus is adapted structurally to be used as an impression tray.

7. A dental apparatus as recited in claim 4, wherein the apparatus is adapted structurally to be used as a fluoride tray.

* * * * *